United States Patent
Matsumura et al.

(10) Patent No.: US 8,669,241 B2
(45) Date of Patent: Mar. 11, 2014

(54) OPHTHALMIC COMPOSITION

(75) Inventors: Yasuko Matsumura, Osaka (JP); Mariyo Kato, Osaka (JP)

(73) Assignee: Rohto Pharmaceutical Co., Ltd., Osaka (JP)

( * ) Notice: Subject to any disclaimer, the term of this patent is extended or adjusted under 35 U.S.C. 154(b) by 204 days.

(21) Appl. No.: 12/591,784

(22) Filed: Dec. 1, 2009

(65) Prior Publication Data

US 2010/0137252 A1 Jun. 3, 2010

Related U.S. Application Data

(60) Provisional application No. 61/193,547, filed on Dec. 5, 2008.

(30) Foreign Application Priority Data

Dec. 2, 2008 (JP) ................................. 2008-307957
Sep. 17, 2009 (JP) ................................. 2009-215467

(51) Int. Cl.
*A61K 31/685* (2006.01)
*A61K 31/045* (2006.01)

(52) U.S. Cl.
USPC .............................. 514/77; 514/724; 514/912

(58) Field of Classification Search
USPC ............................................ 514/77, 724, 912
See application file for complete search history.

(56) References Cited

U.S. PATENT DOCUMENTS

| 5,401,728 A * | 3/1995 | Simon ............................. 514/78 |
| 2005/0080043 A1* | 4/2005 | Shahinian, Jr. .................. 514/57 |
| 2007/0053861 A1* | 3/2007 | Nakayama et al. ........ 424/70.23 |

* cited by examiner

*Primary Examiner* — Zohreh Fay
(74) *Attorney, Agent, or Firm* — Wenderoth, Lind & Ponack, L.L.P.

(57) ABSTRACT

The ophthalmic composition of the invention comprises (A) lecithin and (B) at least one refrigerant selected from the group consisting of camphor, borneol, eucalyptus oil, and bergamot oil. In the ophthalmic composition, the odor of lecithin is efficiently masked by the refrigerant. The odor of lecithin after aging is also masked by the refrigerant. Since the refrigerant is volatile, the concentration thereof in a composition tends to gradually decrease. It is surprising that the odor of lecithin after aging can nevertheless be masked.

9 Claims, No Drawings

OPHTHALMIC COMPOSITION

This application claims the benefit of U.S. provisional application Ser. No. 61/193,547 filed Dec. 5, 2008.

TECHNICAL FIELD

The present invention relates to an ophthalmic composition, a method for masking the odor of lecithin, a method for reducing the cytotoxicity of borneol, and a method for inhibiting oxidation of lecithin.

BACKGROUND ART

Tears coating the eyeball surface have a three-layer structure consisting of a mucous layer comprising mucin, an aqueous layer, and an oily layer, from the eyeball side. Between the aqueous layer and the oily layer, an amphiphilic lecithin layer is known to exist and stabilize tears by acting as a bridge between the two layers (Nihon No Ganka Vol. 74, No. 6, 569-572, 2003).

Since lecithin is a tear constituent, ophthalmic compositions comprising lecithin have been proposed in recent years. For example, WO 2006/009112 discloses an aqueous eyedrop for prevention or treatment of dry eyes, the solution comprising castor oil and lecithin. Also, WO 2005/025539 discloses an ophthalmic composition for contact lenses, the composition comprising a refrigerant and/or chlorobutanol and forming an oil-in-water emulsion due to the presence of lecithin.

SUMMARY OF INVENTION

Technical Problem

Lecithin has a characteristic unpleasant odor. Meanwhile, ophthalmic compositions are required to have high quality as drugs, quasi drugs, or equivalents thereof, from a viewpoint of safety. When lecithin is used as an ingredient of an ophthalmic composition and the composition attaches to the eye, its vicinity, or the hand, the unpleasant odor not only gives discomfort feeling to the patient but also may increase uneasiness about the quality or lower compliance with medication.

A major objective of the present invention is to provide an ophthalmic composition in which the odor of lecithin is masked.

Solution to Problem

The present inventors have wholeheartedly carried out investigations in order to achieve the objective described above and obtained the following findings.
(i) Addition of at least one refrigerant selected from the group consisting of camphor, borneol, eucalyptus oil, and bergamot oil to an ophthalmic composition comprising lecithin effectively masks the odor of lecithin.
(ii) Generally, the odor of lecithin increases with time. Since camphor, borneol, eucalyptus oil, and bergamot oil are volatile, the concentration thereof in a composition tends to decrease with time. Nevertheless, in the above-mentioned ophthalmic composition, the time-depending increase of the odor of lecithin and deterioration of lecithin are effectively inhibited.
(iii) Borneol has cytotoxicity, which is remarkably inhibited by mixing lecithin and borneol.
(iv) An ophthalmic composition comprising lecithin and at least one refrigerant selected from the group consisting of camphor, borneol, eucalyptus oil, and bergamot oil effectively improves eyestrain.
(v) Addition of at least one refrigerant selected from the group consisting of camphor, borneol, eucalyptus oil, and bergamot oil to an ophthalmic composition comprising lecithin inhibits oxidization of lecithin.
(vi) Addition of at least one refrigerant selected from the group consisting of camphor, borneol, eucalyptus oil, and bergamot oil to an ophthalmic composition comprising lecithin enhances the tear-stabilizing effect of lecithin.

The present invention, completed on the basis of the above findings, provides the following ophthalmic compositions, method for masking the odor of lecithin, method for reducing the cytotoxicity of borneol, and method for inhibiting oxidation of lecithin.
(1) An ophthalmic composition comprising:
 (A) lecithin and
 (B) at least one refrigerant selected from the group consisting of camphor, borneol, eucalyptus oil, and bergamot oil.
(2) The ophthalmic composition according to the above-mentioned (1), further comprising a vegetable oil.
(3) The ophthalmic composition according to the above-mentioned (2), wherein the vegetable oil is sesame oil.
(4) The ophthalmic composition according to any of the above-mentioned (1) to (3), further comprising an alcohol.
(5) The ophthalmic composition according to the above-mentioned (4), wherein the alcohol is at least one kind selected from the group consisting of glycerin, propylene glycol, and ethanol.
(6) The ophthalmic composition according to any of the above-mentioned (1) to (5), which is for improving eyestrain.
(7) The ophthalmic composition according to any of the above-mentioned (1) to (5), which is for stabilizing tears.
(8) A method for masking the odor of lecithin, comprising a step of mixing lecithin and at least one refrigerant selected from the group consisting of camphor, borneol, eucalyptus oil, and bergamot oil.
(9) The method according to the above-mentioned (8), wherein the odor of lecithin is the odor after aging.
(10) A method for inhibiting the increase of the odor of lecithin caused by aging, the method comprising a step of mixing lecithin and at least one refrigerant selected from the group consisting of camphor, borneol, eucalyptus oil, and bergamot oil.
(11) A composition in which the odor of lecithin and the odor after aging are inhibited by at least one refrigerant selected from the group consisting of camphor, borneol, eucalyptus oil, and bergamot oil, and mixed with lecithin.
(12) A method for reducing the cytotoxicity of borneol, comprising a step of mixing borneol and lecithin.
(13) A method for inhibiting oxidation of lecithin, comprising a step of mixing lecithin and at least one refrigerant selected from the group consisting of camphor, borneol, eucalyptus oil, and bergamot oil.

Advantageous Effects of Invention

The ophthalmic composition of the present invention, which comprises lecithin and a specific refrigerant, effectively stabilizes the three-layer structure of tears, and therefore is useful as an eyedrop for dry eyes or eye dryness, or in another dosage form. In the ophthalmic composition of the present invention, the unpleasant odor of lecithin is effectively inhibited not only immediately after preparation but also after a long period of time (10 days to 3 years and 6 months). As a result, users do not feel discomfort or uneasiness, and their compliance with medication will be improved.

In the ophthalmic composition of the present invention, the odor of lecithin is masked by camphor, borneol, eucalyptus oil, bergamot oil, or a mixture of two or more kinds thereof, comprised in the composition. Further, in the ophthalmic composition of the present invention, the odor of lecithin after aging is also masked by camphor, borneol, eucalyptus oil, bergamot oil, or a mixture of two or more kinds thereof, comprised as a refrigerant. Since these refrigerants are volatile, the concentration thereof in a composition tends to gradually decrease. It is surprising that the odor of lecithin after aging can nevertheless be masked. The above-mentioned refrigerant can not only mask the odor of lecithin caused by aging, but also inhibit further generation or increase of the odor caused by aging of lecithin. Since the above-mentioned refrigerant effectively inhibits oxidation of lecithin, the inhibition of oxidation is expected to contribute to the inhibition of the increasing odor of lecithin.

The ophthalmic composition of the present invention effectively improves eyestrain or asthenopia, and therefore is useful as an eyedrop for improving eyestrain.

In addition, although the inventors found that borneol is cytotoxic, the cytotoxicity of borneol is remarkably inhibited in the composition of the present invention comprising borneol and lecithin. Therefore, in the ophthalmic composition of the present invention, the odor of lecithin is effectively masked and the cytotoxicity is remarkably inhibited at the same time.

Further, the ophthalmic composition of the present invention, which comprises camphor, borneol, eucalyptus oil, bergamot oil, or a mixture of two or more kinds thereof, in addition to lecithin, has an enhanced tear-stabilizing effect.

DESCRIPTION OF EMBODIMENTS

Hereafter, the present invention will be explained in detail.
(I) Ophthalmic composition The ophthalmic composition of the present invention comprises (A) lecithin and (B) at least one refrigerant selected from the group consisting of camphor, borneol, eucalyptus oil, and bergamot oil. Preferably, the ophthalmic composition of the present invention comprises (A) lecithin and (B) at least one refrigerant selected from the group consisting of camphor and borneol.

Examples of the ophthalmic composition include eyedrop, eyewash, contact lens fitting solution, contact lens care solution (cleaning solution, storage solution, disinfectant solution, and multipurpose solution), preservative for isolated cornea for transplantation, ophthalmic ointment, etc. The ophthalmic composition of the present invention has a high tear-stabilizing effect and safety level, and is excellent in eyestrain improvement effect and compliance improvement effect, and therefore is especially suitable as eyedrop, contact lens fitting solution, or eyewash.
Lecithin The origin of the lecithin is not particularly limited. Examples of the lecithin include egg yolk lecithin, soybean lecithin, cone lecithin, peanut lecithin, rapeseed lecithin, etc. These lecithins may be a nonhydrogenated or hydrogenated lecithin (including completely hydrogenated or slightly hydrogenated lecithin). The iodine value of lecithin is also not particularly limited, and for example, may be 10 or less. The range of the iodine value is preferably about 20 to 100, more preferably about 30 to 90, and still more preferably about 35 to 85. Also, the acid value of lecithin is preferably 50 or less, more preferably 40 or less, and still more preferably 30 or less.

In addition, lecithin comprises phospholipid, such as phosphatidylcholine (PC), phosphatidylethanolamine (PE), phosphatidylinositol (PI) and lysophosphatidylcholine (LPC), and the content of phosphatidylcholine relative to the whole lecithin is preferably 30% or more, more preferably 50% or more, and still more preferably 70% or more by weight. Meanwhile, the content of phosphatidylethanolamine relative to the whole lecithin is preferably 50% or less, more preferably 30% or less, and still more preferably 15% or less by weight. Further, the content of phosphatidylinositol relative to the whole lecithin is preferably 50% or less, more preferably 30% or less, and still more preferably 15% or less by weight. Further, the content of lysophosphatidylcholine relative to the whole lecithin is preferably 20% or less, and more preferably 10% or less by weight. Examples of such a lecithin include Lecinol S-10, Lecinol S-10M, Lecinol S-10E, Lecinol S-10EX, Lecinol S-HSO, Lecinol WS-50 and Lecinol LL-20 by Nikko Chemicals; PL-30S, PL-100M, PC-98N and PL-100P by Q.P.; SLP-PC90, SLP-PC92H, SLP-White, SLP-White SP, SLP-White H, SLP-PC70, SLP-PC70H and SLP-LPC70 by Tsuji Oil Mill; NC-21, NC-21E and NC-61 by NOF; Lipoid E-80 by Lipoid; Epikuron 120 and Ovothin 160 by Lucus Meyer; etc. These lecithins may be used alone or in a combination of two or more thereof.

The content of lecithin, as the total amount of lecithins, relative to the whole ophthalmic composition is preferably about 0.001 to 20% w/v, more preferably about 0.01 to 10% w/v, and still more preferably about 0.05 to 5% w/v. When the lecithin content is within the above-mentioned range, the effects of the present invention, such as sufficient tear-stabilizing effect, can be obtained.
Refrigerant As the refrigerant, at least one kind selected from the group consisting of camphor, borneol, eucalyptus oil, and bergamot oil is used. Two or more kinds thereof also may be used in combination. Preferably, at least one kind selected from the group consisting of camphor and borneol is used. These ingredients may be any of d-isomer, l-isomer and dl-isomer.

The content of the refrigerant in the ophthalmic composition, as the total amount of refrigerants, relative to the whole ophthalmic composition is preferably about 0.0001 to 0.075% w/v, more preferably about 0.0005 to 0.06% w/v, and still more preferably about 0.001 to 0.05% w/v. The content of the refrigerant in the ophthalmic composition relative to 100 parts by weight of lecithin is preferably about 0.05 to 400 parts by weight, more preferably about 0.2 to 200 parts by weight, and still more preferably about 0.4 to 100 parts by weight. When the refrigerant content is within the above-mentioned range, the odor of lecithin can sufficiently be masked, and the ophthalmic composition can be highly safe and less irritant. When the content is within the above-mentioned range, eyestrain can sufficiently be improved. Further, when the content is within the above-mentioned range, oxidation of lecithin can sufficiently be inhibited and the tear-stabilizing effect of lecithin can sufficiently be enhanced.
Oil The ophthalmic composition of the present invention preferably comprises an oil, for example, a vegetable oil; an animal oil such as squalane; a mineral oil such as liquid paraffin and petrolatum; etc. Inter alia, a vegetable oil is preferred. The oil in the ophthalmic composition contributes to further effective masking of the odor of lecithin and further effective improvement of eyestrain. The oil contributes to further enhancement of the tear-stabilizing effect of lecithin, also.

Examples of the vegetable oil include sesame oil, castor oil, soybean oil, olive oil, wheat germ oil, peppermint oil, sunflower seed oil, cotton seed oil, corn oil, palm oil, peanut oil, almond oil, safflower oil, jojoba oil, camellia oil, rape oil, orange oil, etc. Inter alia, because of good feeling in use and effectiveness in the present invention, sesame oil and castor oil which have polarity are preferred, and sesame oil is more preferred. For example, castor oils currently sold by Itoh Oil Chemicals, Nisshin OilliO, etc., and sesame oils currently sold by TAKEMOTO Oil & Fat, Nisshin OilliO, etc. may be used.

These oils may be used alone or in a combination of two or more thereof.

The content of oil, as the total amount of oils, relative to the whole ophthalmic composition is preferably about 0.001 to 10% w/v, more preferably about 0.005 to 5% w/v, and still more preferably about 0.01 to 1% w/v. The content of oil in the whole ophthalmic composition relative to 100 parts by weight of lecithin is preferably about 0.05 to 50,000 parts by weight, more preferably about 0.2 to 10,000 parts by weight, still more preferably about 2 to 5,000 parts by weight, and especially preferably about 2 to 200 parts by weight. When the oil content is within the above-mentioned range, the ophthalmic composition has a sufficient effect of supplying oily layer to tears, and a good feeling in use. Moreover, when the content is within the above-mentioned range, oxidation of lecithin can sufficiently be inhibited, the tear-stabilizing effect of lecithin can sufficiently be enhanced, and other effects of the present invention can be further exerted.

Alcohol

The ophthalmic composition of the present invention preferably comprises an alcohol, which contributes to further effective masking of the odor of lecithin and further effective improvement of eyestrain. Also, the alcohol in the ophthalmic composition contributes to further enhancement of the tear-stabilizing effect of lecithin, and further exertion of other effects of the present invention.

The alcohol may be a polyhydric alcohol or a monohydric alcohol. Examples of the polyhydric alcohol include glycerin, propylene glycol, polyethylene glycol, sorbitol, xylitol, mannitol, etc. Examples of the monohydric alcohol include lower alcohols having 1 to 5 carbon atoms, such as ethanol, propanol, butanol, and pentanol. Glycerin, propylene glycol, and ethanol are preferably used. These alcohols may be used alone or in a combination of two or more thereof.

The content of alcohol, as the total amount of alcohols, relative to the whole ophthalmic composition is preferably about 0.001 to 20% w/v, more preferably about 0.01 to 10% w/v, and still more preferably about 0.05 to 5% w/v. The content of alcohol in the whole ophthalmic composition relative to 100 parts by weight of lecithin is preferably about 0.5 to 50,000 parts by weight, more preferably about 2 to 25,000 parts by weight, still more preferably about 5 to 10,000 parts by weight, and especially preferably about 10 to 5,000 parts by weight. When the alcohol content is within the above-mentioned range, the odor-masking effect of lecithin can sufficiently be enhanced, and the ophthalmic composition has a good feeling in use. Moreover, when the content is within the above-mentioned range, oxidation of lecithin can sufficiently be inhibited, the tear-stabilizing effect of lecithin can be further enhanced, and other effects of the present invention can be further exerted.

Preferable Combinations

Preferable combinations of (A) lecithin, (B) refrigerant, (C) oil and (D) alcohol in the ophthalmic composition of the present invention are shown in Table 1 and Table 2 below.

TABLE 1

| (A) Lecithin | (B) Refrigerant | (C) Oil | (D) Alcohol |
|---|---|---|---|
| Egg-yolk lecithin | Camphor | Sesame oil | Glycerin |
| Egg-yolk lecithin | Camphor | Sesame oil | Propylene glycol |
| Egg-yolk lecithin | Camphor | Sesame oil | Ethanol |
| Egg-yolk lecithin | Camphor | Castor oil | Glycerin |
| Egg-yolk lecithin | Camphor | Castor oil | Propylene glycol |
| Egg-yolk lecithin | Camphor | Castor oil | Ethanol |
| Nonhydrogenated egg-yolk lecithin | Camphor | Sesame oil | Glycerin |
| Nonhydrogenated egg-yolk lecithin | Camphor | Sesame oil | Propylene glycol |
| Nonhydrogenated egg-yolk lecithin | Camphor | Sesame oil | Ethanol |
| Nonhydrogenated egg-yolk lecithin | Camphor | Castor oil | Glycerin |
| Nonhydrogenated egg-yolk lecithin | Camphor | Castor oil | Propylene glycol |
| Nonhydrogenated egg-yolk lecithin | Camphor | Castor oil | Ethanol |
| Hydrogenated egg-yolk lecithin | Camphor | Sesame oil | Glycerin |
| Hydrogenated egg-yolk lecithin | Camphor | Sesame oil | Propylene glycol |
| Hydrogenated egg-yolk lecithin | Camphor | Sesame oil | Ethanol |
| Hydrogenated egg-yolk lecithin | Camphor | Castor oil | Glycerin |
| Hydrogenated egg-yolk lecithin | Camphor | Castor oil | Propylene glycol |
| Hydrogenated egg-yolk lecithin | Camphor | Castor oil | Ethanol |
| Soybean lecithin | Camphor | Sesame oil | Glycerin |
| Soybean lecithin | Camphor | Sesame oil | Propylene glycol |
| Soybean lecithin | Camphor | Sesame oil | Ethanol |
| Soybean lecithin | Camphor | Castor oil | Glycerin |
| Soybean lecithin | Camphor | Castor oil | Propylene glycol |
| Soybean lecithin | Camphor | Castor oil | Ethanol |
| Slightly hydrogenated soybean lecithin | Camphor | Sesame oil | Glycerin |
| Slightly hydrogenated soybean lecithin | Camphor | Sesame oil | Propylene glycol |
| Slightly hydrogenated soybean lecithin | Camphor | Sesame oil | Ethanol |
| Slightly hydrogenated soybean lecithin | Camphor | Castor oil | Glycerin |
| Slightly hydrogenated soybean lecithin | Camphor | Castor oil | Propylene glycol |
| Slightly hydrogenated soybean lecithin | Camphor | Castor oil | Ethanol |
| Hydrogenated soybean lecithin | Camphor | Sesame oil | Glycerin |
| Hydrogenated soybean lecithin | Camphor | Sesame oil | Propylene glycol |
| Hydrogenated soybean lecithin | Camphor | Sesame oil | Ethanol |
| Hydrogenated soybean lecithin | Camphor | Castor oil | Glycerin |
| Hydrogenated soybean lecithin | Camphor | Castor oil | Propylene glycol |
| Hydrogenated soybean lecithin | Camphor | Castor oil | Ethanol |

TABLE 2

| (A) Lecithin | (B) Refrigerant | (C) Oil | (D) Alcohol |
|---|---|---|---|
| Egg-yolk lecithin | Borneol | Sesame oil | Glycerin |
| Egg-yolk lecithin | Borneol | Sesame oil | Propylene glycol |
| Egg-yolk lecithin | Borneol | Sesame oil | Ethanol |
| Egg-yolk lecithin | Borneol | Castor oil | Glycerin |
| Egg-yolk lecithin | Borneol | Castor oil | Propylene glycol |
| Egg-yolk lecithin | Borneol | Castor oil | Ethanol |
| Nonhydrogenated egg-yolk lecithin | Borneol | Sesame oil | Glycerin |
| Nonhydrogenated egg-yolk lecithin | Borneol | Sesame oil | Propylene glycol |
| Nonhydrogenated egg-yolk lecithin | Borneol | Sesame oil | Ethanol |
| Nonhydrogenated egg-yolk lecithin | Borneol | Castor oil | Glycerin |
| Nonhydrogenated egg-yolk lecithin | Borneol | Castor oil | Propylene glycol |
| Nonhydrogenated egg-yolk lecithin | Borneol | Castor oil | Ethanol |
| Hydrogenated egg-yolk lecithin | Borneol | Sesame oil | Glycerin |
| Hydrogenated egg-yolk lecithin | Borneol | Sesame oil | Propylene glycol |
| Hydrogenated egg-yolk lecithin | Borneol | Sesame oil | Ethanol |
| Hydrogenated egg-yolk lecithin | Borneol | Castor oil | Glycerin |
| Hydrogenated egg-yolk lecithin | Borneol | Castor oil | Propylene glycol |
| Hydrogenated egg-yolk lecithin | Borneol | Castor oil | Ethanol |
| Soybean lecithin | Borneol | Sesame oil | Glycerin |
| Soybean lecithin | Borneol | Sesame oil | Propylene glycol |
| Soybean lecithin | Borneol | Sesame oil | Ethanol |
| Soybean lecithin | Borneol | Castor oil | Glycerin |
| Soybean lecithin | Borneol | Castor oil | Propylene glycol |
| Soybean lecithin | Borneol | Castor oil | Ethanol |
| Slightly hydrogenated soybean lecithin | Borneol | Sesame oil | Glycerin |
| Slightly hydrogenated soybean lecithin | Borneol | Sesame oil | Propylene glycol |
| Slightly hydrogenated soybean lecithin | Borneol | Sesame oil | Ethanol |
| Slightly hydrogenated soybean lecithin | Borneol | Castor oil | Glycerin |
| Slightly hydrogenated soybean lecithin | Borneol | Castor oil | Propylene glycol |
| Slightly hydrogenated soybean lecithin | Borneol | Castor oil | Ethanol |
| Hydrogenated soybean lecithin | Borneol | Sesame oil | Glycerin |
| Hydrogenated soybean lecithin | Borneol | Sesame oil | Propylene glycol |
| Hydrogenated soybean lecithin | Borneol | Sesame oil | Ethanol |
| Hydrogenated soybean lecithin | Borneol | Castor oil | Glycerin |
| Hydrogenated soybean lecithin | Borneol | Castor oil | Propylene glycol |
| Hydrogenated soybean lecithin | Borneol | Castor oil | Ethanol |

For stable and efficient exertion of the effects of the present invention, it is also preferred that each composition shown in Tables 1 and 2 further comprises a boric acid buffer (boric acid, borax, sodium salts of boric acid, etc.) and/or an edetate (sodium edetates, etc.) The total content of boric acid buffers may be about 0.1 to 3 w/v %, preferably about 0.5 to 2.5 w/v %, and more preferably about 1 to 2 w/v %. The total content of edetates may be about 0.001 to 0.1 w/v %, preferably about 0.005 to 0.07 w/v %, and more preferably about 0.01 to 0.06 w/v %.

The ophthalmic composition of the present invention may contain common active ingredients (pharmacologically active ingredients, physiologically active ingredients or the like) in addition to the above ingredients. Examples of such ingredients include, but are not limited to, decongestants, drugs for modulating ocular muscles, anti-inflammatory drugs or astringents, antiallergic drugs, vitamins, amino acids, antibacterial drugs or disinfectants, saccharides, polymers or their derivatives, cellulose or its derivatives, local anesthetics, anti-glaucoma drugs and anti-cataract drugs. The pharmacologically active ingredients and physiologically active ingredients preferably used in the present invention include the following ingredients:

Decongestants: for example, alpha-adrenergic drugs such as epinephrine, epinephrine hydrochloride, ephedrine hydrochloride, oxymetazoline hydrochloride, tetrahydrozoline hydrochloride, naphazoline hydrochloride, phenylephrine hydrochloride, methylephedrine hydrochloride, epinephrine bitartrate, naphazoline nitrate or the like, all of which may be in either d-form, l-form or dl-form;

Drugs for modulating ocular muscles: for example, cholinesterase inhibitor with active centers similar to that of acetylcholine, such as neostigmine methylsulfate, tropicamide, helenien, atropine sulfate or the like;

Anti-inflammatory drugs or astringents: for example, zinc sulfate, zinc lactate, allantoin, epsilon-aminocaproic acid, indomethacin, lysozyme chloride, silver nitrate, pranoprofen, sodium azulene sulfonate, dipotassium glycyrrhizinate, diammonium glycyrrhizinate; diclofenac sodium, bromfenac sodium, berberine chloride, berberine sulfate or the like;

Anti-histamine or antiallergic drugs: for example, acitazanolast, diphenhydramine, diphenhydramine hydrochloride, chlorpheniramine maleate, ketotifen fumarate, levocabastine, levocabastine hydrochloride, amlexanox, ibudilast, tazanolast, tranilast, oxatomide, suplatast or its tosilate salts, sodium cromoglycate, pemirolast potassium or the like;

Vitamins: for example, retinol acetate, retinol palmitate, pyridoxine hydrochloride, sodium flavin adenine dinucleotide, pyridoxal phosphate, cyanocobalamin, panthenol, calcium pantothenate, sodium pantothenate, ascorbic acid, tocopherol acetate, tocopheryl nicotinate, tocopheryl succinate, tocopheryl calcium succinate, ubiquinone derivatives or the like;

Amino acids: for example, aminoethylsulfonic acid (taurine), glutamic acid, creatinine, sodium aspartate, potassium aspartate, magnesium aspartate, a mixture of magnesium and potassium aspartates, sodium glutamate, magnesium glutamate, epsilon-aminocaproic acid, glycine, alanine, arginine, lysine, gamma-aminobutyric acid, gamma-aminovaleric acid, sodium chondroitin sulfate or the like, all of which may be in either d-form, l-form or dl-form;

Antibacterial drugs or disinfectants: for example, alkylpolyaminoethylglycine, chloramphenicol, sulfamethoxazole, sulfisoxazole, sulfamethoxazole sodium, sulfisoxazole diethanolamine, sulfisoxazole monoethanolamine, sulfisomezole sodium, sulfisomidine sodium, ofloxacin, norfloxacin, levofloxacin, lomefloxacin hydrochloride; aciclovir or the like;

Saccharides: for example, monosaccharide, disaccharide, and in particular glucose, maltose, trehalose, sucrose, cyclodextrin, xylitol, sorbitol, mannitol or the like;

Polymers or their derivatives: for example, alginic acid, sodium alginate, dextrin, dextran, pectin, hyaluronic acid, chondroitin sulfate, polyvinyl alcohol (completely or partially saponified), polyvinylpyrrolidone, carboxyvinylpolymer, macrogol and its pharmaceutically acceptable salts or the like;

Cellulose or its derivatives: for example, ethyl cellulose, hydroxyethyl cellulose, hydroxypropyl cellulose, hydroxypropylmethyl cellulose, methyl cellulose, carboxymethyl cellulose, sodium carboxymethyl cellulose, carboxyethyl cellulose, nitrocellulose or the like;

Local anesthetics: for example, chlorobutanol, procaine hydrochloride, lidocaine hydrochloride or the like;

The mixing ratio of each ingredient is known in the field of ophthalmic compositions. Thus, the mixing ratios of the above ingredients in the ophthalmic composition of the present invention will be appropriately selected depending on the dosage form of said ophthalmic composition, the types of pharmacologically active ingredients or physiologically active ingredients, and the like. For example, the mixing ratios of pharmacologically active ingredients or physiologically active ingredients can be selected from a range of about 0.0001 to 30 w/v %, preferably about 0.001 to 10 w/v % based on the total amount of the ophthalmic composition.

According to the present invention; one or more kinds can be appropriately selected from other various ingredients and additives depending upon the intended use or form of the ophthalmic composition, and incorporated into the composition according to conventional means, so long as the effect of the invention is not impaired. Examples of these ingredients or additives include carriers generally used for preparing semi-solid or liquid formulations (aqueous solvents, aqueous or oily bases, etc.), and a variety of additives such as surfactants, preservatives, disinfectants or antibacterial drugs, pH adjusters, tonicity agents, chelating agents, buffering agents and stabilizers.

Examples of typical ingredients used in the ophthalmic composition of the present invention include, but are not limited to:

Carriers: for example, aqueous solvent such as water and hydrous ethanol;

Surfactants: for example, nonionic surfactants such as polyoxyethylene (hereinafter referred to as POE)-polyoxypropylene (hereinafter referred to as POP) block copolymer (for example, poloxamer 407), POE-POP block copolymer adduct of ethylene diamine (for example, poloxamine), POE sorbitan fatty acid ester (for example, polysorbate80), POE hydrogenated castor oil (for example, POE(60) hydrogenated castor oil) and polyoxyl stearate; glycine-type amphoteric surfactants such as alkyldiaminoethylglycine; cationic surfactants such as alkyl quaternary ammonium salt (for example, benzalkonium chloride, benzethonium chloride) or the like, with the figure in parentheses representing the number of added moles;

Flavors or refrigerants: for example, terpenoid (for example, anethol, eugenol, geraniol, menthol, limonen, or the like, all of which may be in either d-form, l-form or dl-form), essential oil (mentha water, mentha oil, peppermint oil, rose oil, etc.) or the like;

Preservatives, disinfectants or antibacterial drugs: for example, polydronium chloride, alkyldiaminoethylglycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl parahydroxybenzoate, ethyl parahydroxybenzoate, propyl parahydroxybenzoate, butyl parahydroxybenzoate, oxyquinoline sulfate, phenethyl alcohol, benzyl alcohol, biguanide (e.g., polyhexamethylene biguanide, polyhexamethylene biguanide hydrochloride), Glokill® (Rhodia) or the like;

pH adjusters: for example, hydrochloric acid, sodium hydroxide, potassium hydroxide, calcium hydroxide, magnesium hydroxide, triethanolamine, monoethanolamine, diisopropanolamine, sulfuric acid, polyphosphoric acid, or the like;

Tonicity agents: for example, sodium hydrogen sulfite, sodium sulfite, potassium chloride, calcium chloride, sodium chloride, magnesium chloride, potassium acetate, sodium acetate, sodium hydrogen carbonate, sodium carbonate, sodium thiosulfate, magnesium sulfate, disodium hydrogen phosphate, sodium dihydrogen phosphate, potassium dihydrogen phosphate, glycerin, propylene glycol or the like;

Chelating agents, for example, ascorbic acid; tetrasodium edetate, sodium edetate, citric acid or the like;

Buffering agents: for example, citrate buffer, acetate buffer, carbonate buffer, borate buffer, phosphate buffer, or the like. More specifically, citric acid, sodium citrate, acetic acid, potassium acetate, sodium acetate, sodium hydrogen carbonate, sodium carbonate, boric acid, borax, phosphoric acid, disodium hydrogen phosphate, sodium dihydrogen phosphate, potassium dihydrogen phosphate or the like;

Stabilizers: for example, dibutyl hydroxytoluene, trometamol, sodium formaldehyde sulfoxylate (Rongalite), tocopherol, sodium pyrosulfite, monoethanolamine, aluminum monostearate, glyceryl monostearate, or the like.

These optional ingredients may be used alone or in a combination of two or more thereof.

The ophthalmic composition of the present invention is usually a liquid medicine except when it is an ophthalmic ointment. In a liquid medicine, the content of water is usually 90% w/v or more, and preferably 95% w/v or more.

In the case of an ophthalmic ointment, a publicly known base material for ophthalmic ointment, for example, white petrolatum, liquid paraffin, plastibase, purified lanolin, etc., can be used.

The pH of the ophthalmic composition of the present invention may be about 3 to 9, preferably about 5 to 8, and more preferably about 5.5 to 7.5.

The container into which the ophthalmic composition of the present invention is charged is not particularly limited, and may be a container comprising such a material as polyethylene terephthalate, polyarylate, polycarbonate, polyethylene; and polypropylene, for example. The container is preferably a light-shielding container. The light-shielding container allows the ophthalmic composition of the present invention to be stably stored for a long period of time. The light-shielding effect may be given to the container by the use of a colorant etc. mixed with the above-mentioned material, or by a covering such as a shrink film or an outer casing.

Preparation Method

The ophthalmic composition of the present invention can be prepared by a common method. For example, the composition may be prepared by dispersing each ingredient in one kind or a mixture of two or more kinds selected from the group consisting of water, oils, alcohols and surfactants, then using a homogenizer etc. for homogenization, dissolution or emulsification of the mixture, and then adjusting the pH with a pH adjustor.

Method for Use

The dosage and administration in the case where the ophthalmic composition of the present invention is a liquid medicine or an ophthalmic ointment depends on the patient's condition, age, etc., but usually about 1 or 2 drops at a time may be instilled or an appropriate amount at a time may be applied about 1 to 6 times per day.

In the case where the ophthalmic composition of the present invention is an eyedrop, the subject of administration is not particularly limited, and includes patients suffering from dry eyes, eyestrain, etc. Inter alia, patients suffering from dry eyes, particularly evaporative dry eyes are preferred subjects.

(II) Method for Masking the Odor of Lecithin and Method for Inhibiting the Increase of the Odor of Lecithin The method of the present invention for masking the odor of lecithin comprises a step of mixing lecithin and at least one refrigerant selected from the group consisting of camphor, borneol, eucalyptus oil, and bergamot oil.

The term "mask", as used herein, means eliminating or reducing an odor regardless of the mechanism. The method of the present invention also includes masking the odor of lecithin after aging by mixing lecithin and the above-mentioned refrigerant. As described above, masking the odor of lecithin after aging includes effectively masking odor newly generated by aging. The method comprising a step of mixing lecithin and the above-mentioned refrigerant effectively inhibits not only the odor of lecithin immediately after mixing but also the increase of the odor caused by aging.

The term "aging", as used herein, means leaving the composition under a certain temperature (thermal) condition including inconstant condition such as room temperature or under a photoirradiation condition for a certain period of time. Also, the term "after aging", as used herein, means after a lapse of about 10 days to 3 years and 6 months, preferably about 1 month to 3 years, and more preferably about 6 months to 3 years, or an equivalent period thereof, at room temperature (or room-temperature equivalent after conversion) from suspension or dissolution of lecithin in a solvent such as water. The aging includes aging under either of a light-shielding condition and a non-light-shielding condition.

The method of the present invention can be applied to compositions for all uses which comprise lecithin. The method can be applied to cosmetics, foods and drinks, etc. besides the ophthalmic composition mentioned above.

Examples of the cosmetics include skin toner, milky lotion, cosmetic cream, eye cream, cosmetic gel, cosmetic lotion, face pack, foundation, face wash, body soap, shampoo, hair rinse, hair conditioner, hand cream, makeup products etc.

In masking the odor of lecithin of a composition comprising lecithin, the kind and the dosage of lecithin and the dosage of the refrigerant used are as described for the ophthalmic composition.

In masking the odor of lecithin of a cosmetic, the content of lecithin relative to the whole cosmetic may be about 0.05 to 5% by weight, and the content of the refrigerant relative to the whole cosmetic may be about 0.01 to 6% by weight, although both contents depend on the kind of the cosmetic. The content of the refrigerant in a cosmetic may be about 0.2 to 12,000 parts by weight relative to 100 parts by weight of lecithin. The kind of lecithin is as described for the ophthalmic composition.

In masking the odor of lecithin of a food or drink, the content of lecithin relative to the whole food or drink may be about 0.1 to 5% by weight, and the content of the refrigerant relative to the whole food or drink may be about 0.1 to 1% by weight, although both contents depends on the kind of the food or drink. The content of the refrigerant in a food or drink may be about 2 to 1,000 parts by weight relative to 100 parts by weight of lecithin. The kind of lecithin is as described for the ophthalmic composition.

(III) Method for Reducing the Cytotoxicity of Borneol

The method of the present invention for reducing the cytotoxicity of borneol comprises a step of mixing borneol and lecithin. The "reducing the cytotoxicity", as used herein, includes eliminating the cytotoxicity. The target cells include mucosal cells of the eye, such as corneal cells (in particular corneal epithelial cells) and conjunctiva cells (in particular conjunctival epithelial cells), for example.

The method of the present invention can be applied to compositions for all uses which comprise lecithin. For example, the cytotoxicity of borneol in the above-mentioned ophthalmic composition can be reduced by this method. The kind and the dosage of lecithin and the dosage of borneol used are as described for the ophthalmic composition.

(IV) Method for Inhibiting Oxidation of Lecithin

The method of the present invention for inhibiting the oxidation of lecithin comprises a step of mixing lecithin and at least one refrigerant selected from the group consisting of camphor, borneol, eucalyptus oil, and bergamot oil.

The inhibition of oxidation of lecithin can be judged by measuring the acid value or the peroxide value by a conventional method.

The method of the present invention can be applied to compositions for all uses which comprise lecithin, for example, ophthalmic compositions, cosmetics, and foods and drinks. The kind and the dosage of lecithin and the dosage of the refrigerant used are as described for the ophthalmic composition.

(V) Method for Enhancing the Tear-Stabilizing Effect of Lecithin

The method of the present invention for enhancing the tear-stabilizing effect of lecithin comprises a step of mixing lecithin and at least one kind selected from the group consisting of camphor, borneol, eucalyptus oil, and bergamot oil.

EXAMPLES

Hereinafter, the present invention will be illustrated in detail by Examples, but is not limited thereto.

1. Odor Mask Test

According to the formula shown in Tables 3 to 7 below, each of the eyedrops of Examples 1 to 26 and Comparative Examples 1 to 8 was prepared by a usual preparation method, and charged in a 10 mL container made of polyethylene terephthalate, and then the container was stopped.

TABLE 3

|  | Example 1 | Example 2 | Example 3 | Example 4 | Example 5 | Example 6 | Example 7 | CE 1 | (g/100 mL) CE 2 |
|---|---|---|---|---|---|---|---|---|---|
| Purified egg-yolk lecithin PL-100M | 1 | 1 | 1 | 1 | 1 | 1 | 1 | 1 | 1 |
| D-camphor | 0.015 |  | 0.015 | 0.015 | 0.005 | 0.015 |  |  |  |
| Borneol |  | 0.013 |  |  |  |  | 0.003 |  |  |
| L-menthol |  |  |  |  |  |  |  | 0.015 |  |
| Sesame oil |  |  | 0.025 |  |  | 0.025 |  |  |  |
| Castor oil |  |  |  |  |  |  |  |  |  |
| Glycerin |  |  |  | 1 |  | 1 |  |  |  |
| Boric acid | 1.2 | 1.2 | 1.2 | 1.2 | 1.2 | 1.2 | 1.2 | 1.2 | 1.2 |
| Borax | 0.3 | 0.3 | 0.3 | 0.3 | 0.3 | 0.3 | 0.3 | 0.3 | 0.3 |
| Sodium edetate | 0.05 | 0.05 | 0.05 | 0.05 | 0.05 | 0.05 | 0.05 | 0.05 | 0.05 |
| Purified water | q.s. | q.s. | q.s. | q.s. | q.s. | q.s. | q.s. | q.s. | q.s. |
| Total | 100 mL | 100 mL | 100 mL | 100 mL | 100 mL | 100 mL | 100 mL | 100 mL | 100 mL |

CE: Comparative Example

TABLE 4

|  | Example 8 | Example 9 | Example 10 | Example 11 | Example 12 | Example 13 | CE 3 | CE 4 | (g/100 mL) CE 5 |
|---|---|---|---|---|---|---|---|---|---|
| Purified egg-yolk lecithin PL-100M | 0.05 | 0.05 | 0.05 | 0.05 | 0.05 |  | 0.05 | 0.05 |  |
| Purified egg-yolk lecithin PL-30S |  |  |  |  |  | 0.1 |  |  | 0.1 |
| D-camphor | 0.015 |  | 0.015 | 0.015 | 0.015 |  |  |  |  |
| Borneol |  | 0.013 |  |  |  | 0.005 |  |  |  |
| L-menthol |  |  |  |  |  |  | 0.015 |  | 0.01 |
| Sesame oil |  |  | 0.025 |  | 0.025 |  |  |  |  |
| Glycerin |  |  |  | 1 | 1 |  |  |  |  |
| Boric acid | 1.2 | 1.2 | 1.2 | 1.2 | 1.2 | 0.96 | 1.2 | 1.2 | 0.96 |
| Borax | 0.3 | 0.3 | 0.3 | 0.3 | 0.3 | 0.20 | 0.3 | 0.3 | 0.20 |
| Sodium edetate | 0.05 | 0.05 | 0.05 | 0.05 | 0.05 | 0.04 | 0.05 | 0.05 | 0.04 |
| Purified water | q.s. | q.s. | q.s. | q.s. | q.s. | q.s. | q.s. | q.s. | q.s. |
| Total | 100 mL | 100 mL | 100 mL | 100 mL | 100 mL | 100 mL | 100 mL | 100 mL | 100 mL |

CE: Comparative Example

TABLE 5

|  | Example 14 | Example 15 | Example 16 | Example 17 | CE 6 | (g/100 mL) CE 7 |
|---|---|---|---|---|---|---|
| Purified egg-yolk lecithin PL-100M | 0.1 | 0.1 | 0.1 | 0.1 | 0.1 | 0.1 |
| DL-camphor | 0.04 |  |  |  |  |  |
| Borneol |  | 0.02 |  |  |  |  |
| L-menthol |  |  |  | 0.005 |  |  |
| Eucalyptus oil |  | 0.005 |  |  |  |  |
| Bergamot oil |  |  |  | 0.002 |  |  |
| Propylene glycol | 0.5 | 0.5 | 0.5 | 0.5 | 0.5 | 0.5 |
| Sodium chloride | 0.3 | 0.3 | 0.3 | 0.3 | 0.3 | 0.3 |
| Boric acid | 1.2 | 1.2 | 1.2 | 1.2 | 1.2 | 1.2 |
| Borax | 0.25 | 0.25 | 0.25 | 0.25 | 0.25 | 0.25 |
| Purified water | q.s. | q.s. | q.s. | q.s. | q.s. | q.s. |
| Total | 100 mL | 100 mL | 100 mL | 100 mL | 100 mL | 100 mL |

CE: Comparative Example

TABLE 6

|  | Example 18 | Example 19 | Example 20 | Example 21 | (g/100 mL) Example 22 |
|---|---|---|---|---|---|
| Purified egg-yolk lecithin PL-100M | 1 | 1 | 1 | 1 | 1 |
| D-camphor | 0.01 |  | 0.01 | 0.01 | 0.01 |
| Borneol |  | 0.007 |  |  |  |
| Sesame oil |  |  | 0.05 |  | 0.05 |
| Glycerin |  |  |  | 1 | 1 |
| Boric acid | 1.2 | 1.2 | 1.2 | 1.2 | 1.2 |
| Borax | 0.25 | 0.25 | 0.25 | 0.25 | 0.25 |

TABLE 6-continued

|  | Example 18 | Example 19 | Example 20 | Example 21 | (g/100 mL) Example 22 |
|---|---|---|---|---|---|
| EDTA | 0.05 | 0.05 | 0.05 | 0.05 | 0.05 |
| Purified water | q.s. | q.s. | q.s. | q.s. | q.s. |
| Total | 100 mL | 100 mL | 100 mL | 100 mL | 100 mL |

TABLE 7

|  | Example 23 | Example 24 | Example 25 | Example 26 | (g/100 mL) CE 8 |
|---|---|---|---|---|---|
| Purified egg-yolk lecithin PL-100M | 1 | 1 | 1 | 0.1 | 1 |
| D-camphor | 0.04 | 0.04 | 0.04 | 0.04 | |
| Sesame oil | | 0.05 | | | |
| Glycerin | | | 1 | | |
| Boric acid | 1 | 1 | 1 | 1 | 1 |
| Borax | 0.18 | 0.18 | 0.18 | 0.18 | 0.18 |
| Sodium chloride | 0.3 | 0.3 | 0.3 | 0.3 | 0.3 |
| Purified water | q.s. | q.s. | q.s. | q.s. | q.s. |
| Total | 100 mL | 100 mL | 100 mL | 100 mL | 100 mL |

CE: Comparative Example 1-1. Evaluation of Odor-Masking Effect Before and after Thermal Aging Each of the eyedrops of Examples 1 to 12 and Comparative Examples 1 to 4 was evaluated for odor before (within 1 day after preparation of the eyedrop) and after 10-day thermal aging at 40° C. under a light-shielding condition. One drop of the eyedrop was dropped onto the palm or the back of the hand, and lightly spread with a finger. The unpleasant odor was evaluated using VAS (Visual Analogue Scale), defining the minimum as 0 and the maximum (odor felt after thermal aging in Comparative Example 2) as 6. The results, average ratings of five test subjects, are shown in Tables 8 and 9. Assuming the change at 40° C. in 6 months is equivalent to the change at room temperature in 3 years, thermal aging at 40° C. for 10 days is equivalent to thermal aging at room temperature for about 2 months.

The results show that camphor and borneol have a higher odor-masking effect compared with menthol. In addition, it was confirmed that such an effect was maintained even after thermal aging. Furthermore, it was confirmed that the odor-masking effect of camphor after thermal aging is enhanced by blending sesame oil or glycerin, and further enhanced by blending both sesame oil and glycerin.

In the similar manner, each of the eyedrops of Examples 14 to 17 and Comparative Examples 6 and 7 was evaluated for odor before (within 1 day after preparation of the eyedrop) and after thermal aging at 50° C. for 1 month, at 50° C. for 2 months, at 40° C. for 1 month, at 40° C. for 4 months, and at 40° C. for 7 months, and aging at 25° C. for 1 month, at 25° C. for 4 months, and at 25° C. for 7 months, under a light-shielding condition.

The unpleasant odor was evaluated using VAS (Visual Analogue Scale), defining minimum odor as 0 and maximum odor (odor felt after thermal aging in Comparative Example 7, at 40° C. for 7 months) as 6. The results, average ratings of five test subjects, are shown in Table 10. Assuming aging at 40° C. for 6 months is equivalent to aging at room temperature for 3 years, thermal aging at 50° C. for 1 month, at 50° C. for 2 months, at 40° C. for 1 month, at 40° C. for 4 months, and at 40° C. for 7 months are equivalent to aging at room temperature for about 1 year and 6 months, about 3 years, about 6 month, about 2 years, and about 3 years and 6 months, respectively.

TABLE 10

|  | Example 14 | Example 15 | Example 16 | Example 17 | CE 6 | CE 7 |
|---|---|---|---|---|---|---|
| Before aging | 0 | 0 | 0.6 | 1.4 | 3.8 | 5.6 |
| 50° C., 1 month | 0 | 0.6 | 2.2 | 1.8 | 6.0 | 6.0 |
| 50° C., 2 months | 0.2 | 1.0 | 2.4 | 2.8 | 6.0 | 6.0 |
| 40° C., 1 month | 0 | 0.4 | 1.0 | 2.0 | 1.4 | 5.8 |
| 40° C., 4 months | 0 | 0.4 | 1.2 | 2.6 | 6.0 | 6.0 |
| 40° C., 7 months | 0.2 | 0.6 | 1.8 | 3.0 | 6.0 | 6.0 |
| 25° C., 1 month | 0 | 0.4 | 1.0 | 1.6 | 5.0 | 5.6 |
| 25° C., 4 months | 0 | 0.4 | 1.6 | 2.0 | 5.2 | 5.8 |
| 25° C., 7 months | 0 | 0.6 | 1.8 | 2.0 | 6.0 | 6.0 |
| 25° C., 36 months | 0 | 0.6 | 2.0 | 2.2 | 6.0 | 6.0 |

CE: Comparative Example

The results show that the odor-masking effect of camphor, borneol, eucalyptus oil, or bergamot oil was maintained under any of the above thermal aging or aging conditions. In addi-

TABLE 8

|  | Example 1 | Example 2 | Example 3 | Example 4 | Example 5 | Example 6 | Example 7 | CE 1 | CE 2 |
|---|---|---|---|---|---|---|---|---|---|
| Before aging | 0.4 | 0 | 0.2 | 0.2 | 2.2 | 0 | 0 | 3.6 | 4.4 |
| After thermal aging | 3.4 | 0 | 2.4 | 2.0 | 3.8 | 1.6 | 0.4 | 5.8 | 6.0 |

CE: Comparative Example

TABLE 9

|  | Example 8 | Example 9 | Example 10 | Example 11 | Example 12 | CE 3 | CE 4 |
|---|---|---|---|---|---|---|---|
| Before aging | 0.2 | 0 | 0 | 0.2 | 0 | 2.2 | 3.6 |
| After thermal aging | 2.0 | 0 | 1.6 | 1.2 | 0.8 | 3.5 | 4.6 |

CE: Comparative Example tion, it was found that camphor, borneol, eucalyptus oil, and bergamot oil have a higher odor-masking effect compared with menthol.

1-2. Evaluation of Odor-Masking Effect after Photo-Aging (1)

Each of the eyedrops of Example 13 and Comparative Example 5 was evaluated for odor before (within 1 day after preparation of the eyedrop) and after photo-aging. The photo-aging was performed using a photostability testing device (Light-Tron LT-120 D3CJ manufactured by Nagano Science) with a D65 lamp as the light source. Each solution was irradiated at 4,200 lx at 25° C. to get exposed to cumulative irradiation of 300,000 lx·h. In a condition where the eyedrops of Example 13 and Comparative Example 5 cannot be distinguished from each other by test subjects, one drop of one eyedrop was dropped onto the right hand, and one drop of the other eyedrop was dropped onto the left hand. For evaluation, the two odors were compared and numerically rated according to Table 11 below. Obtained values were averaged. The number of test subjects was 11. Assuming the cumulative irradiation per day is 10,000 lx·h (for example, indoor exposure at 1,000 lx/h for 10 hours per day), cumulative irradiation of 300,000 lx·h is equivalent to about 1-month indoor exposure.

TABLE 11

| | |
|---|---|
| Example 13 has a much stronger odor | −2 |
| Example 13 has a stronger odor | −1 |
| Example 13 and Comparative Example 5 have the same level of odor | 0 |

TABLE 11-continued

| | |
|---|---|
| Comparative Example 5 has a stronger odor | 1 |
| Comparative Example 5 has a much stronger odor | 2 |

The averaged value was 1.0, which showed that the eyedrop of Comparative Example 5 smelled worse than the eyedrop of Example 13. The results show that even after photo-aging, the odor-masking effect of borneol was higher than that of menthol.

1-3. Evaluation of Odor-Masking Effect after Photo-Aging (2)

Each of the eyedrops of Examples 27 to 62 and Comparative Examples 9 to 22 shown in Tables 12 to 17 below, in an amount of 13 mL was charged in a 13-mL container made of polyethylene terephthalate, and was evaluated for odor before (within 1 day after preparation of the eyedrop) and after photo-aging. The photo-aging was performed using a photostability testing device (Light-Tron LT-120 D3CJ manufactured by Nagano Science) with a D65 lamp as the light source. Each solution was irradiated at 25° C. at 4,000 lx/h for 18 days and 18 hours to get exposed to cumulative irradiation of 1,800,000 lx·h. This cumulative irradiation is equivalent to indoor photo-aging for six months.

One drop of the eyedrop was dropped onto the palm or the back of the hand, and lightly spread with a finger. The unpleasant odor was evaluated using VAS (Visual Analogue Scale), defining minimum odor as 0 and maximum odor (odor felt after photo-aging in Comparative Example 9) as 10. The ratings of five test subjects were averaged. The results are shown in Tables 12 to 17.

TABLE 12

| | | | | | | | | | | | (g/100 mL) |
|---|---|---|---|---|---|---|---|---|---|---|---|
| | Example 27 | Example 28 | Example 29 | Example 30 | Example 31 | Example 32 | Example 33 | Example 34 | Example 35 | Example 36 | Example 37 |
| Purified egg-yolk lecithin PL-100M | 0.1 | 0.1 | 0.1 | 0.1 | 0.1 | 0.1 | 0.1 | 0.1 | 0.1 | 0.1 | 0.1 |
| D-camphor | 0.02 | 0.001 | 0.02 | 0.02 | 0.02 | 0.02 | 0.02 | 0.02 | 0.02 | 0.02 | 0.02 |
| *Eucalyptus* oil | | | | | | | | | | | |
| Bergamot oil | | | | | | | | | | | |
| Sesame oil | | | 0.1 | 0.001 | | | | | | | |
| Castor oil | | | | | 0.1 | 0.001 | | | | | |
| Petrolatum | | | | | | | 0.1 | 0.01 | | | |
| Propylene glycol | | | | | | | | | 1 | 0.1 | |
| Glycerin | | | | | | | | | | | 1 |
| Ethanol | | | | | | | | | | | |
| Purified water | q.s. | q.s. | q.s. | q.s. | q.s. | q.s. | q.s. | q.s. | q.s. | q.s. | q.s. |
| Total | 100 mL | 100 mL | 100 mL | 100 mL | 100 mL | 100 mL | 100 mL | 100 mL | 100 mL | 100 mL | 100 mL |
| Before photo-aging | 1 | 1.3 | 1 | 1 | 1 | 1 | 1 | 1 | 1 | 1 | 1 |
| After photo-aging | 1.5 | 2.1 | 1 | 1.4 | 1 | 1.4 | 1.5 | 1.7 | 1 | 1.2 | 1 |

The results show that a vegetable oil or an alcohol comprised in addition to lecithin and camphor contributed to further effective masking of the odor after photo-aging.

TABLE 13

| | | | | | | | | (g/100 mL) |
|---|---|---|---|---|---|---|---|---|
| | Example 38 | Example 39 | Example 40 | Example 41 | Example 42 | Example 43 | Example 44 | Example 45 |
| Purified egg-yolk lecithin PL-100M | 0.1 | 0.1 | 0.1 | 0.1 | 0.1 | 0.1 | 0.1 | 0.1 |
| D-camphor | 0.02 | 0.02 | 0.02 | 0.02 | 0.02 | 0.01 | 0.01 | 0.01 |
| *Eucalyptus* oil | | | | | | | | |
| Bergamot oil | | | | | | | | |
| Sesame oil | | | | 0.1 | 0.1 | 0.1 | 0.1 | |

TABLE 13-continued

|  | Example 38 | Example 39 | Example 40 | Example 41 | Example 42 | Example 43 | Example 44 | (g/100 mL) Example 45 |
|---|---|---|---|---|---|---|---|---|
| Castor oil | | | | | | | | |
| Petrolatum | | | | | | | | |
| Propylene glycol | | | | 1 | | | 0.5 | |
| Glycerin | 0.1 | | | | 1 | | | |
| Ethanol | | 0.15 | 0.05 | | | | | |
| Purified water | q.s. | q.s. | q.s. | q.s. | q.s. | q.s. | q.s. | q.s. |
| Total | 100 mL | 100 mL | 100 mL | 100 mL | 100 mL | 100 mL | 100 mL | 100 mL |
| Before photo-aging | 1 | 1 | 1 | 1 | 1 | 1.2 | 1 | 1.2 |
| After photo-aging | 1.2 | 1 | 1.2 | 1 | 1 | 1.5 | 1.2 | 1.8 |

Comparison of Example 43 and Example 44 shows that an alcohol comprised in addition to lecithin, camphor and vegetable oil contributed to further effective masking of the odor after photo-aging.

TABLE 14

|  | Example 46 | Example 47 | Example 48 | Example 49 | Example 50 | Example 51 | Example 52 | Example 53 | Example 54 | (g/100 mL) Example 55 |
|---|---|---|---|---|---|---|---|---|---|---|
| Purified egg-yolk lecithin PL-100M | 0.1 | 0.1 | 0.1 | 0.1 | 0.1 | 0.1 | 0.1 | 0.1 | 0.1 | 0.1 |
| D-camphor | | | | | | | | | | |
| *Eucalyptus* oil | 0.005 | 0.001 | 0.005 | 0.005 | 0.005 | | | | | |
| Bergamot oil | | | | | | 0.002 | 0.001 | 0.002 | 0.002 | 0.002 |
| Sesame oil | | | 0.1 | | 0.1 | | | 0.1 | | 0.1 |
| Castor oil | | | | | | | | | | |
| Petrolatum | | | | | | | | | | |
| Propylene glycol | | | | 1 | 1 | | | | 1 | 1 |
| Glycerin | | | | | | | | | | |
| Ethanol | | | | | | | | | | |
| Purified water | q.s. | q.s. | q.s. | q.s. | q.s. | q.s. | q.s. | q.s. | q.s. | q.s. |
| Total | 100 mL | 100 mL | 100 mL | 100 mL | 100 mL | 100 mL | 100 mL | 100 mL | 100 mL | 100 mL |
| Before photo-aging | 1 | 1.7 | 1 | 1 | 1 | 1.3 | 1.3 | 1.2 | 1.2 | 1.2 |
| After photo-aging | 2 | 2.7 | 1.7 | 1.7 | 1.5 | 2.2 | 2.8 | 2 | 1.8 | 1.7 |

The results show that eucalyptus oil or bergamot oil comprised as a refrigerant in addition to lecithin contributed to effective masking of the odor after photo-aging.

TABLE 15

|  | Example 56 | Example 57 | Example 58 | Example 59 | Example 60 | Example 61 | (g/100 mL) Example 62 |
|---|---|---|---|---|---|---|---|
| Purified egg-yolk lecithin PL-100M | 0.1 | 0.1 | 0.1 | 0.1 | 0.1 | 0.1 | 0.1 |
| D-borneol | 0.02 | 0.01 | 0.001 | 0.01 | 0.01 | 0.01 | 0.01 |
| *Eucalyptus* oil | | | | | | | |
| Bergamot oil | | | | | | | |
| Sesame oil | | | | 0.05 | | 0.05 | 0.05 |
| Castor oil | | | | | | | |
| Petrolatum | | | | | | | |
| Propylene glycol | | | | | 0.5 | 0.5 | |
| Glycerin | | | | | | | 0.5 |
| Ethanol | | | | | | | |
| Purified water | q.s. | q.s. | q.s. | q.s. | q.s. | q.s. | q.s. |
| Total | 100 mL | 100 mL | 100 mL | 100 mL | 100 mL | 100 mL | 100 mL |
| Before photo-aging | 1 | 1 | 1.2 | 1 | 1 | 1 | 1 |

TABLE 15-continued

|  | Example 56 | Example 57 | Example 58 | Example 59 | Example 60 | Example 61 | (g/100 mL) Example 62 |
|---|---|---|---|---|---|---|---|
| After photo-aging | 2 | 2.2 | 2.7 | 1.8 | 2 | 1.3 | 1.7 |

The results show that borneol comprised as a refrigerant in addition to lecithin contributed to effective masking of the odor after photo-aging.

TABLE 16

|  | CE 9 | CE 10 | CE 11 | CE 12 | CE 13 | CE 14 | CE 15 | CE 16 | CE 17 | (g/100 mL) CE 18 |
|---|---|---|---|---|---|---|---|---|---|---|
| Purified egg-yolk lecithin PL-100M | 0.1 | 0.1 | 0.1 | 0.1 | 0.1 | 0.1 | 0.1 | 0.1 | 0.1 | 0.1 |
| D-camphor |  | 0.02 | 0.02 | 0.02 | 0.02 | 0.02 | 0.02 | 0.02 | 0.02 | 0.02 |
| Eucalyptus oil |  |  |  |  |  |  |  |  |  |  |
| Bergamot oil |  |  |  |  |  |  |  |  |  |  |
| Sesame oil |  |  | 0.1 |  |  |  |  | 0.1 | 0.1 | 0.1 |
| Castor oil |  |  |  | 0.1 |  |  |  |  |  |  |
| Petrolatum |  |  |  |  |  |  |  |  |  |  |
| Propylene glycol |  |  |  |  | 1 |  |  | 1 |  |  |
| Glycerin |  |  |  |  |  | 1 |  |  | 1 |  |
| Ethanol |  |  |  |  |  |  | 0.15 |  |  | 0.15 |
| Purified water | q.s. | q.s. | q.s. | q.s. | q.s. | q.s. | q.s. | q.s. | q.s. | q.s. |
| Total | 100 mL | 100 mL | 100 mL | 100 mL | 100 mL | 100 mL | 100 mL | 100 mL | 100 mL | 100 mL |
| Before photo-aging | 5.2 | 2.8 | 2.7 | 2.5 | 3.5 | 2.3 | 4.2 | 3 | 2.8 | 4 |
| After photo-aging | 10 | 7.6 | 7.4 | 8.3 | 7.1 | 8.1 | 7.6 | 7 | 6.9 | 6.3 |

CE: Comparative Example

In the Comparative Examples 19 to 22 in Table 17 below, a refrigerant (d-camphor, eucalyptus oil, bergamot oil, or d-borneol) was added to the eyedrops after photo-aging.

Comparison of Example 27 and Comparative Example 19 (camphor), Example 46 and Comparative Example 20 (eucalyptus oil), Example 51 and Comparative Example 21 (bergamot oil), and Example 56 and Comparative Example 22 (borneol) shows that the latter in which the refrigerant was added after aging had a remarkably higher odor rating after aging than the former in which the refrigerant was added before aging, and therefore that these refrigerants inhibited the increase of the odor of lecithin caused by aging.

TABLE 17

|  | CE 19 | CE 20 | CE 21 | (g/100 mL) CE 22 |
|---|---|---|---|---|
| Purified egg-yolk lecithin PL-100M | 0.1 | 0.1 | 0.1 | 0.1 |
| D-camphor | 0.02 |  |  |  |
| Eucalyptus oil |  | 0.005 |  |  |
| Bergamot oil |  |  | 0.002 |  |
| D-borneol |  |  |  | 0.02 |
| Sesame oil |  |  |  |  |
| Castor oil |  |  |  |  |
| Petrolatum |  |  |  |  |
| Propylene glycol |  |  |  |  |
| Glycerin |  |  |  |  |
| Ethanol |  |  |  |  |
| Purified water | q.s. | q.s. | q.s. | q.s. |
| Total | 100 mL | 100 mL | 100 mL | 100 mL |
| Before photo-aging | — | — | — | — |
| After photo-aging | 8.3 | 2.7 | 6.2 | 5.8 |

CE: Comparative Example

2. Cytotoxicity Test

To each well of a 96-well cell culture plate (Corning), $5.0 \times 10^3$ cells of a rabbit corneal epithelial cell line (SIRC) were seeded, and cultured at 37° C., 5% $CO_2$ and 90% humidity for 2 days. Next, the solutions of Examples 27 and 28, and Comparative Example 9 were prepared by dissolving purified egg-yolk lecithin, purified soybean lecithin, and/or borneol in Medium199 (GIBCO) according to the concentrations shown in Table 18 below. Subsequently, the solutions were separately added to the wells, and culture was performed for 24 hours. To the control wells, Medium199 was added. After culture, the supernatant was removed, Medium199 containing 10% v/v of a viable cell detection reagent, Cell Counting Kit-8 (Dojindo Laboratories), was added, and incubation was performed at 37° C., 5% $CO_2$ and 90% humidity for 1 hour. After the 1-hour incubation, the absorbance at 450 nm was measured with a spectrophotometer (Thermo Electron), based on color development of dye in response to viable cells. The relative cell survival rate was calculated with the use of the following Formula 1. The results are shown in Table 19.

TABLE 18

|  | Example 27 | Example 28 | CE 9 |
| --- | --- | --- | --- |
| Purified egg-yolk lecithin PL-100M | 0.1 | — | — |
| Purified soybean lecithin SLP-PC92H | — | 0.1 | — |
| Borneol | 0.03 | 0.03 | 0.03 |

CE: Comparative Example

Relative cell survival rate(%)=(absorbance in a solution-treated well-absorbance of the mixture of the culture medium and the viable cell detection reagent)/(absorbance in the control well-absorbance of the mixture of the culture medium and the viable cell detection reagent)×100    Formula 1

TABLE 19

|  | Example 27 | Example 28 | CE 9 |
| --- | --- | --- | --- |
| Relative cell survival rate (%) | 95 | 112 | 41 |

CE: Comparative Example

The relative cell survival rate in the well treated with the solution of Comparative Example 9 was low, showing that borneol is cytotoxic. In contrast, the relative cell survival rates in the wells treated with the solution of Example 27 or 28 were high, showing that lecithin reduced the cytotoxicity of borneol. Also, these higher relative cell survival rates show that the cells in the wells treated with the solution of Example 27 or 28 were equally viable to, or more viable than the control cells. These results revealed that the cytotoxity-reducing effect of lecithin against borneol is excellent.

3. Acid Value Evaluation Test

According to the formula shown in Table 3, each of the eyedrops of Examples 1 and 3 and Comparative Examples 1 and 2 was prepared by a usual preparation method, and charged in a 10 mL transparent glass ampule. Each of these eyedrops was measured for acid value, according to Eisei Shikenhou Chukai 2000, 2.1.4.3 Alteration Test, 3) Acid Value Test Method, before and after photo-aging. The photo-aging was performed using a photostability testing device (Light-Tron LT-120 D3CJ manufactured by Nagano Science) with a D65 lamp as the light source. Each solution was irradiated by ultraviolet light at 4,200 lx at 25° C. to get exposed to cumulative irradiation of 180,000 lx·h. The change in the acid value caused by photo-aging was calculated by subtracting the acid value before photo-aging from that after photo-aging. Assuming the cumulative irradiation per day is 10,000 lx·h (for example, indoor exposure at 1,000 lx/h for 10 hours per day), cumulative irradiation of 180,000 lx·h is equivalent to about 18-day indoor exposure. The results are shown in Table 20 below.

TABLE 20

|  | Example 1 | Example 3 | CE 1 | CE 2 |
| --- | --- | --- | --- | --- |
| Acid value before photo-aging | 0.262 | 0.254 | 0.256 | 0.253 |
| Amount of acid value change | −0.002 | −0.008 | 0.035 | 0.049 |

CE: Comparative Example

The eyedrops of Examples 1 and 3, and Comparative Examples 1 and 2 showed an equivalent acid value before photo-aging. The acid values of the eyedrops of Comparative Examples 1 and 2 were raised by photo-aging whereas those of Examples 1 and 3 were not. Thus, it was confirmed that camphor inhibited the rise of the acid value of eyedrops comprising lecithin.

4. Flicker Value Measurement Test

Before and after instilling each of the eyedrops of Examples 18 to 22 and Comparative Example 1, the flicker value was measured, and the improvement rate was calculated according to the following Formula 2 (n=3). The results are shown in Table 21. The flicker value is defined as the critical frequency at which a flickering light, of which the frequency is gradually raised, becomes indistinguishable from a steady, non-flickering light to the naked eye. Using the flicker value as an index, eyestrain and/or decrease of perceptual functions can be measured. Therefore, the improvement in flicker values is an objective index of the improvement of eyestrain (especially those resulting from physical and/or mental fatigue with decreased perceptual functions) and asthenopia.

Improvement rate(%)=(flicker value immediately after instillation−flicker value before instillation)/flicker value before instillation×100    Formula 2

TABLE 21

|  | Example 18 | Example 19 | Example 20 | Example 21 | Example 22 | CE 1 |
| --- | --- | --- | --- | --- | --- | --- |
| Improvement rate (%) | 0.7 | 0.4 | 1.8 | 2.1 | 4.4 | −3.2 |

CE: Comparative Example

The results show that in Comparative Example 1, where the eyedrop comprised menthol in addition to lecithin, improvement in flicker values was not observed, whereas eyedrops comprising camphor or borneol in addition to lecithin improved flicker values (Examples 18 and 19). Also, it was confirmed that eyedrops further comprising sesame oil or glycerin brought increased improvement rates (Examples 20 and 21) and that eyedrops further comprising both sesame oil and glycerin brought a further increased improvement rate (Example 22).

5. Tear Stability Evaluation

The stability of tear was evaluated according to Tear Stability Analysis System (TSAS) for dry eye patients. In particular, an auto ref-topographer (TOMEY RT-6000 by TOMEY) and a tear stability analysis software TSAS (by TOMEY) were used for evaluation. The auto ref-topographer and the tear stability analysis software TSAS were used according to the attached instructions thereof.

First, before instillation, while the eye of each subject was kept open for 10 seconds, Mayer ring images of the cornea were captured at 1-second intervals using TSAS. The tear breakup time and the breakup area of the images were visualized as color code maps or breakup maps to evaluate tear stability. In addition, BUI (breakup index) for each subject, which was calculated based on the color code area at each second, which is estimated to be tear breakup area, and elapsed time, was used for evaluation. Subsequently, the eyedrops of Examples 23, 24, 25 and 26, and Comparative Example 8 were instilled to test subjects. In the same manner as the above, 15 minutes after instillation, while the eye of each subject was kept open for 10 seconds, Mayer ring images of the cornea were captured at 1-second intervals using TSAS to obtain breakup maps, and then resulting BUI was used for evaluation. Test subjects were selected from those who showed BUI in the range of 60 to 80 before instillation (n=1).

The obtained breakup maps showed that the tear stability after instillation of the eyedrop of Example 23 was significantly higher as compared in the case of Comparative Example 8, demonstrating that camphor enhanced the tear-stabilizing effect of lecithin. Further, the obtained breakup maps showed that, after instillation of the eyedrop of Example 24 or 25, the tear stability was higher as compared in the case of Example 23, demonstrating that sesame oil and glycerin augmented the effect of camphor enhancing the tear-stabilizing effect.

The BUI results are shown in Table 22.

TABLE 22

|  | Example 23 | Example 24 | Example 25 | Example 26 | CE 8 |
|---|---|---|---|---|---|
| BUI before instillation | 78.354 | 72.804 | 69.361 | 77.773 | 76.261 |
| BUI after instillation | 96.589 | 94.012 | 98.697 | 91.008 | 83.963 |
| Increase in BUI | 18.2 | 21.2 | 29.3 | 13.2 | 7.7 |

CE: Comparative Example

The increase in BUI resulting from instillation of the eyedrop of Example 23 was significantly higher as compared in the case of Comparative Example 8, demonstrating, like the results of breakup maps, that camphor enhanced the tear-stabilizing effect of lecithin. Further, the increase in BUI resulting from instillation of the eyedrop of Example 24 or 25, demonstrated that sesame oil and glycerin augmented the effect of camphor enhancing the tear-stabilizing effect.

6. Formulation Example

Formulation examples will be shown below, but the present invention is not limited thereto.

TABLE 23

|  | Formulation Example (g/100 mL) | | | | |
|---|---|---|---|---|---|
|  | 1 Eyedrop | 2 Eyedrop | 3 Eyedrop | 4 Eyedrop | 5 Eyedrop |
| Purified egg-yolk lecithin PL-100M | 0.005 | 0.01 | 0.1 | 1 | 2 |
| D-camphor | 0.006 | 0.008 | 0.003 | 0.004 | 0.01 |
| Borneol |  |  |  | 0.008 |  |
| L-menthol | 0.005 | 0.005 | 0.015 | 0.01 | 0.02 |
| Geraniol |  |  | 0.005 |  |  |
| *Eucalyptus* oil |  |  |  |  | 0.005 |
| Bergamot oil |  |  |  | 0.002 |  |
| Cool mint |  | 0.012 |  |  |  |
| Mentha oil | 0.016 |  |  |  |  |
| Sesame oil |  | 0.005 | 0.01 | 0.8 | 1 |
| Castor oil | 0.05 |  |  |  |  |
| Glycerin | 0.5 | 0.2 |  | 0.5 |  |
| Propylene glycol |  | 0.2 | 1 |  | 3 |
| Aminoethylsulfonic acid |  | 1 |  | 0.5 |  |
| Sodium chloride | 0.2 | 0.4 | 0.3 | 0.3 | 0.5 |
| Potassium chloride | 0.05 | 0.08 | 0.01 | 0.2 | 0.1 |
| Sodium hydrogen carbonate | 0.01 | 0.15 | 0.3 | 0.15 | 0.3 |
| HEC |  | 0.05 | 0.02 | 0.1 | 0.2 |
| HPMC | 0.05 | 0.5 | 0.02 | 0.3 | 0.1 |
| Boric acid | 1 | 1.1 | 1.2 | 1 | 1 |
| Borax | 0.01 | 0.08 | 0.3 | 0.15 | 0.2 |
| Sodium edetate | 0.05 | 0.01 | 0.05 | 0.1 | 0.1 |
| Poloxamer | 0.1 | 0.04 | 0.05 | 0.1 | 0.01 |
| Xylitol |  | 0.5 |  |  |  |
| Chlorobutanol |  |  |  |  | 0.01 |
| Alpha-cyclodextrin |  | 0.1 |  |  |  |
| Purified water | q.s. | q.s. | q.s. | q.s. | q.s. |
| Total | 100 mL | 100 mL | 100 mL | 100 mL | 100 mL |

TABLE 24

Formulation Examples 6 to 12 (continue to Table 25)

|  | Formulation Example (g/100 mL) | | | | | | |
|---|---|---|---|---|---|---|---|
|  | 6 Eyedrop | 7 Eyedrop | 8 Eyedrop | 9 Eyedrop | 10 Eyedrop | 11 Eyedrop | 12 Eyedrop |
| Purified egg-yolk lecithin PL-100M | 0.1 |  |  |  |  | 0.15 |  |

TABLE 24-continued

Formulation Examples 6 to 12 (continue to Table 25)

(g/100 mL)

| | Formulation Example | | | | | | |
|---|---|---|---|---|---|---|---|
| | 6 Eyedrop | 7 Eyedrop | 8 Eyedrop | 9 Eyedrop | 10 Eyedrop | 11 Eyedrop | 12 Eyedrop |
| Purified egg-yolk lecithin PC-98N | | 0.05 | | | | | |
| Purified soybean lecithin SLP-PC92H | | | 0.2 | | | | |
| Purified soybean lecithin S-10M | | | | 0.1 | | | 0.8 |
| Purified soybean lecithin S-10EX | | | | | 0.1 | | |
| D-camphor | 0.007 | 0.01 | | 0.001 | 0.005 | | |
| DL-camphor | | | | | | 0.01 | 0.005 |
| Borneol | 0.002 | 0.01 | 0.005 | | | | |
| L-menthol | 0.008 | | 0.03 | | 0.015 | 0.006 | |
| Geraniol | | | | 0.003 | | | |
| Eucalyptus oil | | | | | 0.002 | 0.002 | 0.001 |
| Bergamot oil | | | 0.005 | | | | |
| Cool mint | | | | 0.01 | | 0.005 | |
| Mentha oil | 0.008 | | | | | | |
| Sesame oil | 0.005 | | | 0.01 | 0.08 | | |
| Castor oil | | 0.01 | 0.1 | | | 0.08 | 0.03 |
| Glycerin | 0.01 | 0.05 | | | 2.5 | | 0.1 |
| Propylene glycol | 0.05 | | 0.5 | 5 | | | |
| Ethanol | | 0.1 | 1 | | | | 0.5 |
| Aminoethylsulfonic acid | 0.1 | | 0.3 | | | | |
| Sodium chloride | 0.15 | 0.01 | 0.5 | 0.22 | 0.005 | 0.5 | 0.1 |
| Potassium chloride | 0.05 | 0.001 | 0.01 | 0.08 | 0.001 | 0.1 | 0.01 |
| Sodium hydrogen carbonate | 0.4 | | 0.25 | 0.5 | 0.05 | | |
| Sodium hydrogen phosphate | | 0.5 | | | | | |
| Sodium dihydrogen phosphate | | 0.01 | | | | | |
| PVA | | 1 | | | | | |
| PVP | | | | | 1.5 | | |
| Glucose | | 0.1 | | | | | 0.01 |
| Sodium chondroitin sulfate | 0.05 | | | 0.5 | | | 0.025 |
| L-potassium aspartate | 0.5 | 1 | | | 0.5 | | |
| HEC | | 0.02 | | 0.6 | | | |
| HPMC | | | 0.2 | | 0.02 | | |

TABLE 25

Formulation Examples 6 to 12 (continue from Table 24)

(g/100 mL)

| | Formulation Example | | | | | | |
|---|---|---|---|---|---|---|---|
| | 6 Eyedrop | 7 Eyedrop | 8 Eyedrop | 9 Eyedrop | 10 Eyedrop | 11 Eyedrop | 12 Eyedrop |
| MC | 0.01 | | | | | | |
| Calcium chloride | | 0.001 | | | | | |
| Magnesium sulfate | | | 0.001 | | | | |
| Boric acid | 0.8 | | 0.5 | 1 | 0.87 | 1 | 0.7 |
| Borax | 0.01 | | 0.03 | 0.2 | 0.008 | 0.2 | 0.08 |
| Sodium edetate | 0.05 | 0.02 | | 0.05 | | 0.008 | |
| Hyaluronic acid | 0.005 | | 0.1 | 0.001 | 0.3 | | 0.01 |
| Alginic acid | | 0.05 | | | | | |
| TO-10MV | 0.08 | | | | | 0.02 | |
| HCO-60 | | | | 0.1 | | 0.02 | |
| Poloxamer | | 0.1 | | 0.05 | | | 0.08 |
| Dextran 70 | | | | | | 0.1 | |
| L-sodium glutamate | | | | | | 0.15 | |
| Chlorobutanol | | | | 0.4 | | | |
| Polyhexanide hydrochloride | | | 1 ppm | | | | |
| Polydronium chloride | | | | | | | 0.001 |
| Chlorhexidine gluconate | | 0.005 | | | | 0.005 | |
| BHT | | 0.005 | | | | | |
| Potassium sorbate | | | | | 0.1 | | |
| Citric acid | | | | | | 0.1 | |
| Trometamol | | | | | | | 1 |
| Purified water | q.s. | q.s. | q.s. | q.s. | q.s. | q.s. | q.s. |
| Total | 100 mL | 100 mL | 100 mL | 100 mL | 100 mL | 100 mL | 100 mL |

TABLE 26

Formulation Examples 13 to 19 (continue to Table 27)

(g/100 mL)

| | Formulation Example | | | | | | |
|---|---|---|---|---|---|---|---|
| | 13 Eyedrop | 14 Eyedrop | 15 Eyedrop | 16 Eyedrop | 17 Eyedrop | 18 Eyedrop | 19 Eyedrop |
| Purified egg-yolk lecithin PL-100M | 0.1 | | | | | | |
| Purified egg-yolk lecithin PC-98N | | 0.2 | | | | | |
| Purified soybean lecithin SLP-PC92H | | | 0.1 | | | 1.2 | |
| Purified soybean lecithin S-10M | | | | 1.2 | | | 1 |
| Purified soybean lecithin S-10EX | | | | | 0.005 | | |
| D-camphor | 0.01 | 0.003 | | 0.01 | 0.005 | 0.008 | |
| DL-camphor | | | | | | | 0.005 |
| Borneol | | | 0.004 | 0.001 | | | |
| L-menthol | | | | 0.005 | 0.008 | 0.015 | 0.01 |
| Geraniol | 0.005 | | | | | 0.001 | 0.001 |
| Eucalyptus oil | | | 0.003 | | 0.005 | | |
| Bergamot oil | 0.003 | 0.005 | | | | 0.001 | 0.001 |
| Cool mint | | | | 0.001 | | 0.001 | 0.001 |
| Mentha oil | | 0.005 | | | 0.01 | 0.001 | |
| Sesame oil | 0.015 | 0.2 | | 0.8 | 0.008 | 0.25 | 0.5 |
| Castor oil | | | 0.08 | | | 0.25 | |
| Glycerin | 1 | | | | 0.6 | 0.3 | 0.1 |
| Propylene glycol | | 0.5 | 1 | 2.5 | | 0.35 | 0.5 |
| Aminoethylsulfonic acid | | | | 1 | | 0.1 | |
| Sodium chloride | 0.1 | | | | | | |
| Sodium hydrogen carbonate | | 0.1 | | 0.01 | | | 0.01 |
| Tetrahydrozoline hydrochloride | | 0.01 | | | | | 0.01 |
| Naphazoline hydrochloride | | | 0.002 | | | | |
| Neostigmine methylsulfate | 0.005 | | | | | 0.0025 | 0.0050 |
| Epsilon-aminocaproic acid | 0.2 | | | | | 1 | |
| Allantoin | | | | 0.3 | | | |
| Berberine chloride | | | | | | 0.02 | |
| Sodium azulene sulfonate | | | 0.15 | | 0.02 | | |
| Dipotassium glycyrrhizate | | | | | 0.125 | | |
| Zinc sulfate | | | 0.01 | | | | |
| Lysozyme chloride | | | | | 0.01 | | |
| Chlorpheniramine maleate | 0.015 | | | | | 0.03 | |
| FAD | | 0.05 | | | | | |
| Cyanocobalamine | | | | 0.02 | | | |
| Retinol palmitate | | | | | | | 10000 IU |
| Pyridoxine hydrochloride | 0.1 | | | | 0.1 | 0.01 | 0.05 |
| Panthenol | | | 0.05 | 0.1 | | | |
| Tocopheryl acetate | 0.025 | | | | 0.05 | 0.05 | |
| Sodium cromoglicate | | 0.1 | | | | | |

TABLE 27

Formulation Examples 13 to 19 (continue from Table 26)

(g/100 mL)

| | Formulation Example | | | | | | |
|---|---|---|---|---|---|---|---|
| | 13 Eyedrop | 14 Eyedrop | 15 Eyedrop | 16 Eyedrop | 17 Eyedrop | 18 Eyedrop | 19 Eyedrop |
| Boric acid | 0.9 | 0.5 | 1 | 0.5 | 1.2 | 1 | 0.5 |
| Borax | 0.18 | 0.02 | 0.18 | 0.025 | 0.3 | 0.15 | 0.02 |
| Sodium edetate | 0.1 | | | | | | |
| TO-10MV | 0.100 | | | 0.2 | | 0.05 | 0.1 |
| HCO-60 | 0.050 | | | 0.1 | | 0.3 | 0.1 |
| Dextran 70 | | | | 0.01 | | | |
| Benzalkonium chloride | 0.02 | | | | 0.01 | | 0.005 |
| Chlorobutanol | | 0.05 | | | | 0.2 | |
| Polyhexanide hydrochloride | | | | | | 0.1 ppm | |
| Polydronium chloride | | | | | | | |
| Chlorhexidine gluconate | | | 0.005 | | | | |
| BHT | | | | | | | 0.005 |
| Alpha-cyclodextrin | 0.500 | | | 0.05 | | | |
| Citric acid | | | | 0.1 | | | |
| Fennel oil | | 0.005 | | | | | |
| Trometamol | | | | | 0.01 | | |

TABLE 27-continued

Formulation Examples 13 to 19 (continue from Table 26)

(g/100 mL)

| | Formulation Example | | | | | | |
|---|---|---|---|---|---|---|---|
| | 13 Eyedrop | 14 Eyedrop | 15 Eyedrop | 16 Eyedrop | 17 Eyedrop | 18 Eyedrop | 19 Eyedrop |
| Human serum albumin | | | | | | 0.005 | |
| Purified water | q.s. | q.s. | q.s. | q.s. | q.s. | q.s. | q.s. |
| Total | 100 mL | 100 mL | 100 mL | 100 mL | 100 mL | 100 mL | 100 mL |

TABLE 28

Formulation Examples 20 to 24 (continue to Table 29)

(g/100 mL)

| | Formulation Example | | | | |
|---|---|---|---|---|---|
| | 20 Eyewash | 21 Eyewash | 22 Eyewash | 23 Eyewash | 24 Eyewash |
| Purified egg-yolk lecithin PL-100M | 1.5 | | | | |
| Purified egg-yolk lecithin PC-98N | | 0.1 | | | |
| Purified soybean lecithin SLP-PC92H | | | 1 | | |
| Purified soybean lecithin S-10M | | | | 1 | |
| Purified soybean lecithin S-10EX | | | | | 0.1 |
| D-camphor | 0.01 | 0.02 | 0.006 | | |
| Borneol | | | | 0.008 | 0.005 |
| L-menthol | 0.008 | 0.015 | 0.005 | 0.001 | |
| Geraniol | | | | | 0.005 |
| Eucalyptus oil | | | 0.001 | | |
| Bergamot oil | 0.001 | | | | 0.005 |
| Cool mint | | 0.001 | | | 0.006 |
| Mentha oil | | 0.005 | | | 0.01 |
| Sesame oil | | 0.01 | | 0.001 | |
| Castor oil | 0.5 | | 0.1 | | 0.001 |
| Glycerin | | 1 | 0.1 | | 1 |
| Propylene glycol | | 1 | | | 1 |
| Aminoethylsulfonic acid | 0.1 | 0.1 | 0.01 | | 0.01 |
| Sodium chloride | 0.1 | 0.1 | | | |
| Potassium chloride | | | | 0.08 | |
| Sodium hydrogen carbonate | | 0.005 | | 0.005 | 0.1 |
| Sodium hydrogen phosphate | | | | 0.05 | |
| PVP | | | 0.1 | | 0.01 |
| Glucose | | 0.02 | | | |
| Sodium chondroitin sulfate | | 0.01 | | | |
| L-potassium aspartate | 0.01 | 0.01 | 0.01 | 0.1 | |
| HEC | | 0.1 | | 0.05 | |
| HPMC | 0.001 | 0.1 | | | |
| Epsilon-aminocaproic acid | 0.1 | | 0.2 | 0.1 | |
| Dipotassium glycyrrhizate | 0.005 | 0.025 | | | 0.01 |
| Zinc sulfate | | 0.005 | 0.005 | | |
| Chlorpheniramine maleate | 0.001 | 0.003 | | | 0.03 |
| FAD | 0.005 | | | | |
| Cyanocobalamine | | 0.002 | | | |
| Pyridoxine hydrochloride | 0.001 | 0.005 | 0.01 | | 0.01 |
| Panthenol | | | | 0.001 | |
| Tocopheryl acetate | 0.001 | 0.005 | 0.001 | 0.005 | |

TABLE 29

Formulation Examples 20 to 24 (continue from Table 28)

| Formulation Example | 20 Eyewash | 22 Eyewash | 22 Eyewash | 23 Eyewash | 24 Eyewash (g/100 mL) |
|---|---|---|---|---|---|
| Boric acid | 0.4 | 1.5 | 0.8 | 1.2 | 1 |
| Borax | 0.01 | 0.4 | 0.01 | 0.2 | 0.2 |
| Sodium edetate | 0.05 | 0.1 | 0.1 | | 0.004 |
| Hyaluronic acid | | 0.001 | | | |
| Alginic acid | | 0.01 | | 0.01 | |
| TO-10MV | 0.1 | 0.1 | 0.2 | 0.1 | 0.2 |
| HCO-60 | | 0.05 | | | |
| Poloxamer | | 0.01 | 0.05 | 0.001 | |
| Benzalkonium chloride | | 0.004 | | | |
| Chlorobutanol | | 0.01 | 0.001 | | |
| Fennel oil | | | 0.01 | | 0.01 |
| Purified water | q.s. | q.s. | q.s. | q.s. | q.s. |
| Total | 100 mL | 100 mL | 100 mL | 100 mL | 100 mL |

TABLE 30

Formulation Examples 25 to 29

| Formulation Example | 25 Fitting solution | 26 Fitting solution | 27 Fitting solution | 28 Fitting solution | 29 Fitting solution (g/100 mL) |
|---|---|---|---|---|---|
| Purified egg-yolk lecithin PL-100M | 1 | | | | |
| Purified egg-yolk lecithin PC-98N | | 1 | | | |
| Purified soybean lecithin SLP-PC92H | | | 2 | | |
| Purified soybean lecithin S-10M | | | | 0.5 | |
| Purified soybean lecithin S-10EX | | | | | 1 |
| DL-camphor | 0.01 | 0.008 | 0.01 | 0.001 | 0.005 |
| Borneol | | | | 0.005 | 0.008 |
| L-menthol | 0.015 | 0.01 | 0.005 | 0.008 | |
| Geraniol | 0.005 | 0.005 | 0.003 | 0.001 | 0.005 |
| Glycerin | 0.1 | 0.01 | 0.5 | 0.6 | 0.1 |
| Propylene glycol | 0.1 | 1 | 0.8 | 0.4 | 1 |
| Aminoethylsulfonic acid | 0.01 | | 0.1 | 0.1 | |
| Sodium chloride | 0.3 | 0.2 | 0.2 | 0.3 | |
| Potassium chloride | 0.05 | 0.08 | 0.01 | 0.01 | |
| Sodium hydrogen carbonate | 0.1 | 0.02 | | 0.2 | 0.002 |
| PVP | 1 | | 0.1 | 0.1 | |
| Glucose | | 0.01 | | | |
| Sodium chondroitin sulfate | 0.05 | | | | 0.5 |
| L-potassium aspartate | | | | 0.1 | |
| HEC | 0.01 | | 0.1 | | 0.05 |
| HPMC | | 0.01 | | 0.1 | |
| Boric acid | 0.8 | 0.5 | 0.5 | 0.5 | 0.8 |
| Borax | 0.1 | 0.05 | 0.08 | 0.05 | 0.09 |
| Sodium edetate | 0.05 | 0.004 | 0.1 | 0.05 | |
| TO-10MV | | | | | 0.1 |
| HCO-60 | | 0.1 | | | |
| Poloxamer | 0.05 | 0.1 | | 0.05 | 0.1 |
| Polyhexanide hydrochloride | | 0.1 ppm | | | |
| Purified water | q.s. | q.s. | q.s. | q.s. | q.s. |
| Total | 100 mL | 100 mL | 100 mL | 100 mL | 100 mL |

In Tables 24 to 30, PVA represents polyvinyl alcohol; PVP represents polyvinyl pyrrolidone; HEC represents hydroxyethyl cellulose; HPMC represents hydroxypropyl methylcellulose; TO-10MV represents polysorbate 80 made by Nihon Surfactant Kogyo; HCO-60 represents NIKKOL HCO-60, polyoxyethylene hydrogenated castor oil made by Nikko Chemicals; FAD represents flavin adenine dinucleotide sodium; and BHT represents dibutylhydroxytoluene.

INDUSTRIAL APPLICABILITY

The ophthalmic composition of the present invention, which comprises lecithin and a refrigerant, effectively stabilizes the three-layer structure of tears, and therefore is useful as an eyedrop for dry eyes. The composition is an excellent composition in which, although lecithin is comprised, the odor is effectively inhibited not only immediately after production but for a long period of time.

What is claimed is:

1. An ophthalmic composition comprising:
   (A) lecithin at a concentration of 0.05-5 w/v %,
   (B) at least one refrigerant selected from the group consisting of camphor and borneol at a concentration of 0.001-0.05 w/v %,
   (C) at least one alcohol selected from the group consisting of glycerin, propylene glycol, polyethylene glycol, sorbitol, xylitol, mannitol, ethanol, propanol, butanol, and pentanol at a concentration of 0.05-5 w/v %, and
   (D) vegetable oil at a concentration of 0.01-1 w/v %
   with the proviso that the composition excludes chlorobutanol.

2. The ophthalmic composition according to claim 1, wherein the vegetable oil is sesame oil or castor oil.

3. The ophthalmic composition according to claim 1, wherein the alcohol is at least one kind selected from the group consisting of glycerin, propylene glycol, and ethanol.

4. A method for inhibiting the increase of the odor of lecithin caused by aging, the method comprising a step of mixing (A), (B), (C) and (D) as defined in claim 1 to obtain an ophthalmic composition,
   wherein the obtained composition comprises (A) at a concentration of 0.05-5 w/v %, (B) at a concentration of 0.001-0.05 w/v %, (C) at a concentration of 0.05-5 w/v %, and (I)) at a concentration of 0.01-1 w/v %,
   with the proviso that the composition excludes chlorobutanol,
   wherein the increase of the odor of lecithin caused by aging is inhibited.

5. A method for reducing the cytotoxicity of borneol, comprising a step of mixing (A), (B), (C) and (D) as defined in claim 1 to obtain an ophthalmic composition,
   wherein the refrigerant is borneol,
   wherein the obtained composition comprises (A) at a concentration of 0.05-5 w/v %, (B) at a concentration of 0.001-0.05 w/v %, (C) at a concentration of 0.05-5 w/v %, and (D) at a concentration of 0.01-1 w/v %,
   with the proviso that the composition excludes chlorobutanol, and
   wherein the cytotoxicity of borneol is reduced.

6. A method for inhibiting oxidation of lecithin, comprising a step of mixing (A), (B), (C) and (D) as defined in claim 1 to obtain an ophthalmic composition, wherein the obtained composition comprises (A) at a concentration of 0.05-5 w/v %, (B) at a concentration of 0.001-0.05 w/v %, (C) at a concentration of 0.05-5 w/v %, and (D) at a concentration of 0.01-1 w/v %,
   with the proviso that the composition excludes chlorobutanol,
   wherein the oxidation of lecithin is inhibited.

7. A method for improving eyestrain, comprising a step of administering the composition as defined in claim 1, to an eye of a human, wherein eyestrain is improved.

8. A method for treating dry eye, comprising a step of administering the composition as defined in claim 1 to an eye of a human, wherein dry eye is treated.

9. A method for stabilizing three-layer structure of tear, comprising a step of administering the composition as defined in claim 1 to an eye of a human, wherein three-layer structure of tear is stabilized.

* * * * *